United States Patent
Hammond et al.

(12)

(10) Patent No.: US 6,764,983 B1
(45) Date of Patent: Jul. 20, 2004

(54) ANTIOXIDANT COMPOSITIONS AND INDUSTRIAL FLUIDS CONTAINING SAME

(75) Inventors: Earl G. Hammond, Ames, IA (US); Yongyi Julia Jiang, St. Paul, MN (US)

(73) Assignee: Iowa State University Research Foundation, Ames, IA (US)

( * ) Notice: Subject to any disclaimer, the term of this patent is extended or adjusted under 35 U.S.C. 154(b) by 0 days.

(21) Appl. No.: 10/187,184

(22) Filed: Jul. 1, 2002

Related U.S. Application Data

(60) Provisional application No. 60/302,023, filed on Jun. 29, 2001.

(51) Int. Cl.[7] ..................... C10M 135/10; C07C 309/28
(52) U.S. Cl. ....................... 508/403; 508/151; 508/491; 558/52
(58) Field of Search ............................... 508/403, 151, 508/491; 558/52, 403

(56) References Cited

U.S. PATENT DOCUMENTS

| | | | |
|---|---|---|---|
| 3,401,222 A | * 9/1968 | Haynes ........................ 514/517 |
| 4,820,430 A | 4/1989 | Farng et al. |
| 4,828,733 A | 5/1989 | Farng et al. |
| 5,023,361 A | * 6/1991 | Massonneau et al. ......... 558/32 |
| 5,171,461 A | 12/1992 | Di Biase et al. |
| 5,368,776 A | * 11/1994 | Schafer et al. .............. 252/395 |
| 5,520,830 A | 5/1996 | Klaus et al. |
| 5,863,872 A | 1/1999 | Garmier |
| 5,990,055 A | 11/1999 | Garmier |
| 6,121,477 A | * 9/2000 | Yasohara et al. ............. 558/52 |

FOREIGN PATENT DOCUMENTS

| | | |
|---|---|---|
| EP | 0709447 A1 | 1/1996 |
| WO | WO 95/25781 | 9/1995 |

OTHER PUBLICATIONS

Slotboom et al, Synthesis of isomeric lysophosphatides, Recueil des travaux Chimiques des Pays–Bas (1963), 82, 469–86 (Abstract).*

"Soluble copper with sulphur containing phenols to provide oxidation control for lubricating oil compositions," Research Disclosure, 335115, Mar. 1992.

Jiang Y. and Hammond E., "A New and Effective Antioxidant for Vegetable Oils in Industrial Application", 92nd AOCS Annual Meeting & Expo, 2001 Annual Meeting Abstracts. P S89.

* cited by examiner

Primary Examiner—Jerry D. Johnson
(74) Attorney, Agent, or Firm—Quarles & Brady LLP

(57) ABSTRACT

The present invention provides new compounds that can be used as antioxidants for either molecules that do not conation ester groups or esters of alcohols that contain two or more ester groups per molecule wherein at least two of the ester groups are on adjacent carbons in the alcohol moiety. Copper ions can enhance the antioxidization activity of the new compounds. Compositions containing one of the new compound and methods of using the new compounds are disclosed.

43 Claims, 9 Drawing Sheets

US 6,764,983 B1

ANTIOXIDANT COMPOSITIONS AND INDUSTRIAL FLUIDS CONTAINING SAME

CROSS-REFERENCE TO RELATED APPLICATION

This application claims the benefit of U.S. provisional patent application Serial No. 60/302,023, filed on Jun. 29, 2001, which is herein incorporated by reference in its entirety.

STATEMENT REGARDING FEDERALLY SPONSORED RESEARCH OR DEVELOPMENT

BACKGROUND OF THE INVENTION

Because of the poor biodegradability of petroleum-based fluids, elevated petroleum cost and the finite supply of petroleum, there is a growing interest in using vegetable oils for industrial applications. For example, soybean oil (SBO) has been used as a lubricant SBO is bio-degradable. This reduces disposal cost and long-term liability risks, especially in applications where lubricants are lost directly into the environment (1). Furthermore, the low toxicity and high flash point of SBO create a safer working environment for operators. SBO has better anti-wear properties, high viscosity index and low acidity; SBO is more protective to equipment and performs equally well or sometimes even better than traditional petroleum-based oils. A vegetable-based crankcase oil containing 10% to 20% SBO was tested in automobiles, and its performance was reported to meet industry standards. A 1970 Ford Mustang logged more than 26,000 miles with no breakdowns using a crankcase oil containing SBO (2). Biosoy, a hydraulic fluid made from SBO, has been tested in various equipment including garbage trucks and city buses since 1995, and its anti-wear properties for the high-pressure hydraulic systems meet or exceed conventional hydraulic fluid requirements (3, 4).

The use of many vegetable oils in the applications described above has a drawback due to their susceptibility to rapid oxidization. The oxidation causes a polymerization of the triglycerides and increases the viscosity dramatically, thus severely shortening the life of SBO-based lubricants and hydraulic fluids. Researchers have tried various ways to solve this problem, including developing oleate-enriched soybean lines (5) and concentrating oleate in ordinary SBO by urea fractionation. Ruger and Harnmond (6) tested the effectiveness of antioxidants to prevent viscosity increase in SBO at 105° C. (typical temperature condition during industrial use of a lubricant) with bubbling air in the presence of colloidal iron and copper metal. Several antioxidants tested were effective in preventing viscosity increase in SBO with tertiary butylhydroquinone (TBHQ) working the best. Addition of citric acid slightly enhanced the effectiveness of TBHQ. Other antioxidants, especially those that are more effective than TBHQ in preventing oxidization and hence polymerization and viscosity increase in vegetable oils, are desirable.

BRIEF SUMMARY OF THE INVENTION

The present invention provides new compounds that can be used as antioxidants for either molecules that do not contain ester groups or esters of alcohols that contain two or more ester groups per molecule wherein at least two of the ester groups are on adjacent carbons in the alcohol moiety. The above molecules for which the new compounds of the present invention can act as antioxidants are referred to as target molecules in the specification. Copper ions can enhance the antioxidization activity of the new compounds. One can add one of the new compounds and optionally, a copper-containing compound, into an industrial fluid containing a target molecule to inhibit the oxidization of the target molecule. Compositions that contain one of the new compounds and optionally, a copper-containing compound, are within the scope of the present invention. Industrial fluids that contain a target molecule, one of the new compounds and optionally, copper ions, are also within the scope of the present invention.

It is an advantage of the present invention that the new compounds in combination with copper ions are more effective than most other antioxidant systems in inhibiting the oxidization of target molecules.

Other objects, advantages, and features of the present invention will become apparent from the following detailed description of the invention.

DETAILED DESCRIPTION OF THE INVENTION

Figure 1:
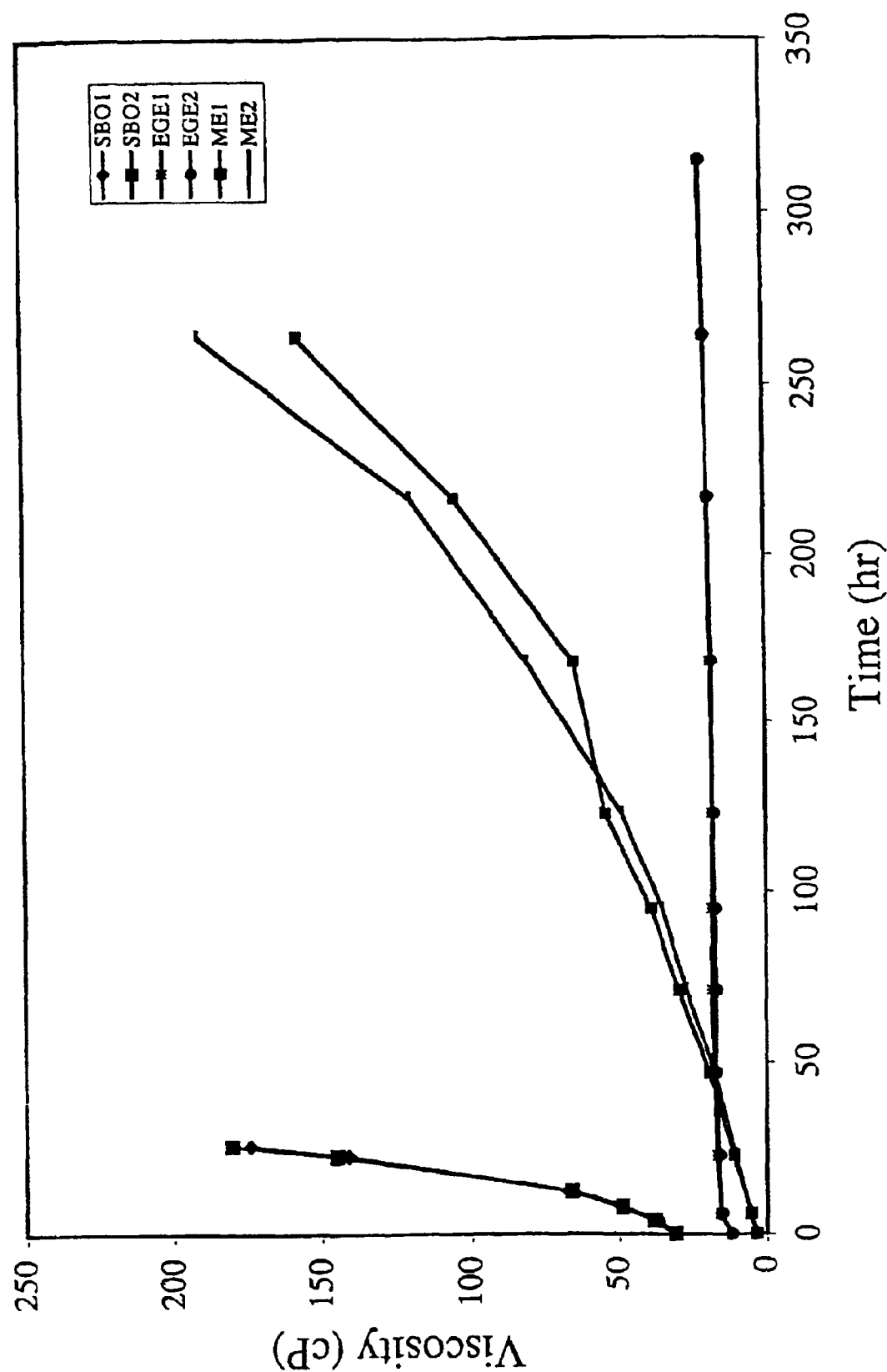
FIG. 1 shows change in viscosity with time of SBO and methyl (ME) and ethylene glycol esters (EGE) made from soybean oil fatty acids. Conditions: 20 ml samples at 105° C. in bubbling air at 2.33 ml/sec plus 10 mg colloidal copper metal.

The present invention provides new compounds that can be added to fluids that contain a target molecule to inhibit the oxidization of the target molecule. The term "inhibit" used in the specification and claims means either partial or complete inhibition. As mentioned earlier, the target molecules of the new compounds of the present invention are either molecules that do not contain ester groups or esters of alcohols that contain two or more ester groups per molecule wherein at least two of the ester groups are on adjacent carbons in the alcohol moiety. Examples of target molecules include but are not limited to molecules in hydrocarbon fluids, triacyl glycerols, diacyl ethylene glycols and diacyl 1,2-propylene glycols. Many industrial fluids contain at least one of the target molecules whose oxidization can adversely affect the functionality of the industrial fluids. The new compounds of the present invention can be used as additives to these industrial fluids. For example, unsaturated triglyceride oils have been used more and more, either alone or in combination with other fluids, as lubricants and hydraulic fluids. The new compounds of the present invention can be used to inhibit the oxidization of these unsaturated triglyceride oils. Examples of these unsaturated triglyceride oils include but are not limited to vegetable oils such as soybean oil, animal oils such as fish oil, and high oleate triglyceride oils.

The new compounds of the present invention are represented by the following formula:

FORMULA 1

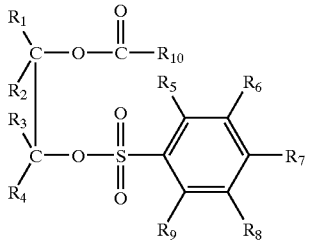

wherein $R_1$–$R_{10}$ are either hydrogen or a carbon chain; the carbon chain can be saturated, unsaturated, linear, branched, cyclic, or polycyclic; the carbon chain can have heteroatoms attached; and the carbon chain of $R_{10}$ is of one to 30 carbons. Examples of heteroatoms that can attach to the carbon chain of $R_1$–$R_{10}$ include but are not limited to N, S, O and Cl. Thus, $R_1$–$R_{10}$ can be alcohols, imides, amides, amines and so on.

In one preferred embodiment, $R_1$–$R_9$ of the compounds of formula 1 are selected from hydrogen, an alkyl group, an alkenyl group, an alkynyl group, an alcohol group and an aromatic group wherein each of $R_5$–$R_9$ has less than 13 carbons; and $R_{10}$ is selected from hydrogen, an alkyl group, an alkenyl group, an alkynyl group and an alcohol group.

In another preferred embodiment, $R_1$ and $R_3$ are hydrogen; one of $R_2$ and $R_4$ is hydrogen or —$CH_2OH$ and the other is hydrogen; $R_{10}$ is an alkyl or alkenyl group of 10 to 18 carbons; and one of $R_5$–$R_9$ is hydrogen or an alkyl group of less than 13 carbons and the others are hydrogen.

In another preferred embodiment, the compound is ethanediol fatty acylate p-toluenesulfonate, EFAT.

A compound of formula 1 can be used either alone, or along with copper, preferably cupric ions, to inhibit the oxidization of target molecules. When being added either alone or in conjunction with a copper-containing compound into an industrial fluid, the final concentration of the compound of formula 1 relative to the total volume of the target molecules in the industrial fluid should be at least about 40 mM, preferably at least about 60 mM, and most preferably at least about 100 mM. The term "about" used before a specific concentration of the compound of formula 1 or copper encompasses small variations of the stated concentration that have a comparable antioxidization effect to the specific concentration.

Any copper-containing compound that can provide cupric or cuprous ions after being added into an industrial fluid that contains a target molecule can be used along with the compounds of formula 1 to inhibit the oxidization of the target molecule. Examples of copper-containing compounds that can be used in the present invention include but are not limited to metal copper, colloidal metallic copper, cupric acetate and other cupric or cuprous salts. Any amount of cupric or cuprous ions can help. Some target fluids such as unsaturated triglyceride oils may contain cupric or cuprous ions in the first place. However, the amount is usually very small and additional amount is necessary for optimal antioxidization enhancement effect. A machine part that is made of copper may also release copper molecules into an industrial fluid that comes in contact with the part. Preferably, for enhancing the antioxidization activity of the compounds of formula 1, the final copper ion concentration relative to the total volume of the target molecules in an industrial fluid is at least about 0.001 mM, more preferably at least about 0.01 mM, 0.1 mM, 0.5 mM or 1.0 mM. A skilled artisan knows how much various suitable copper-containing compounds to use in order to achieve the concentrations described above.

When a compound of formula 1 and a suitable copper-containing compound are added into an industrial fluid to inhibit the oxidization of a target molecule, they can be added separately or as a mixture. The mixture itself is within the scope of the present invention. An industrial fluid that contains a target molecule such as unsaturated triglyceride oil, a compound of formula 1, and optionally copper ions wherein the compound of formula 1 and copper ions are in an amount suitable for inhibiting the oxidization of the target molecule is also within the scope of the present invention.

It is well within the capability of a skilled artisan to make the compounds represented by formula 1. One method of making a specific formula 1 compound, EFAT, is described in the example below. Other compounds represented by formula 1 can be made similarly. Other methods of making the compounds represented by formula 1 that are known to a skilled artisan can also be used.

Figure 7:
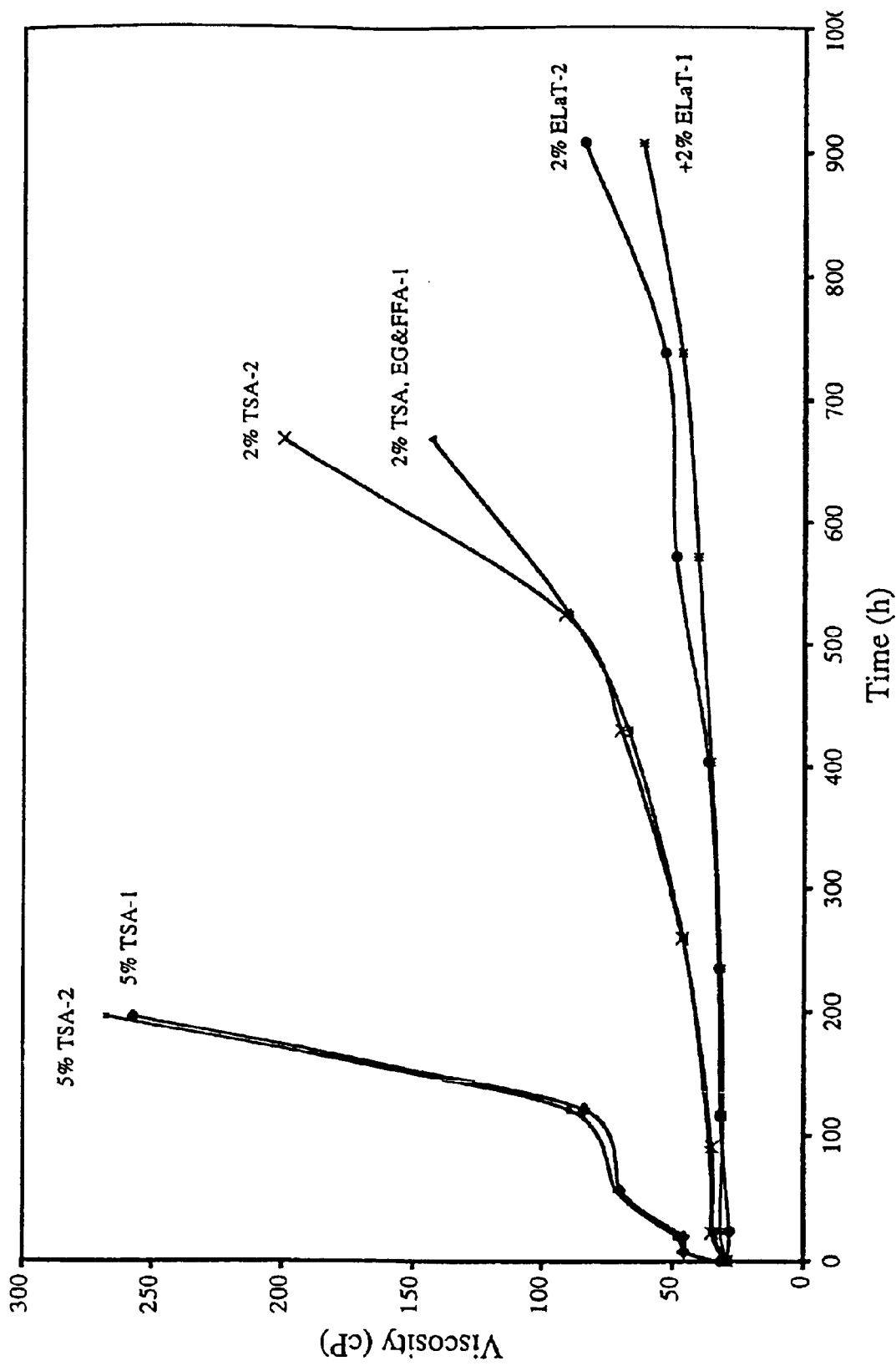
FIG. 7 shows change in viscosity with time of soybean oil containing 5% TSA, the ingredients for making 2% EFAT (TSA, ethylene glycol (EG) & free fatty acids (FFA)), and 2% preformed EFAT. Conditions as in FIG. 1.

It is understood that an industrial fluid that contains a target molecule such as unsaturated triglyceride oil is sometimes used under conditions that allow the formation of a compound of formula 1 from a carboxylic acid, a polyalcohol in which at least two of the hydroxy groups are on adjacent carbon atoms, and an aromatic sulfonate. A skilled artisan knows about these conditions. In these occasions, the present invention can be practiced by adding to the fluid one, two or all three starting materials listed above that are not present in the fluid in sufficient amount so that a compound of formula 1 is formed during the actual use of the fluid. FIG. 7 and related text in the example below illustrates such a situation.

The invention will be more fully understood upon consideration of the following non-limiting example.

EXAMPLE

Materials and Methods

Materials. Refined commercial soybean oil (Crisco, Procter & Gamble, Cincinnati, OH) was purchased from a local grocery store. Unless otherwise specified, the solvents and reagents were purchased from Fisher Scientific (Fair Lawn, N.J.) and were certified grade. Colloidal copper and iron and ethyl p-toluenesulfonate were purchased from Aldrich (St Louis, Mo.).

Synthesis of esters. Soybean oil was converted to methyl esters by mixing 500 ml of oil with 55 g of methanol and 15 g of 5.4 M sodium methoxide (Fluka, Milwaukee, Wis.) at room temperature for 15 h. The product was washed with water and dried with sodium sulfate.

To make ethylene glycol esters, 500 ml of oil was mixed with 130 g potassium hydroxide, 750 ml water, and 25 ml ethanol and stored at 70° C. under nitrogen for 16 h. Next, 200 ml of 12 N hydrochloric acid was added, and the free fatty acids (FFA) were recovered and dried with sodium sulfate. The FFA and ethylene glycol were reacted in a 2.04:1, molar ratio in refluxing benzene for 18 h with p-toluenesulfonic acid (TSA) at 1.5% by the weight of the FFA as a catalyst. A Dean-Stark trap was used to remove the water of esterification. The milliliters of benzene were set at 2.5 times the weight of the fatty acid plus 30 ml to fill the leg of the Dean-Stark trap. The reaction mixture was neutralized with 5% aqueous sodium carbonate solution, washed gently with water five times and the benzene was removed with a rotary evaporator (Buchi, Flawil, Swizerland). Ethylene glycol monoacyl ester of soybean oil FFA was produced by the same method using a 3:1 molar ratio of ethylene glycol to FFA.

Ethylene glycol fatty acylate p-toluenesulfonate (EFAT) was synthesized with various fatty acids (lauric, palmitic, stearic, linoleic, and linolenic) using a molar ratio of ethylene glycol: TSA: FFA of 1:1:1 and using refluxing benzene and a Dean-Stark trap to remove the water of esterification as before. Excess TSA was removed by washing with sodium carbonate solution. The same method was used to make esters using 1,2- and 1,3-propylene glycol in place of ethylene glycol. To make the decyl ester of TSA, the molar ratio of decanol to TSA 1:1 was used. To substitute glycerol for etheylene glycol, the molar ratio of glycerol:TSA: FFA 1:2:1 was used.

Stability measurement. Oxidative stability was measured in duplicate using the apparatus described for the Active Oxygen Method (AOM) in the American Oil Chemists' Society Method Cd-12–57 (7). Air was supplied by an aquarium pump and was regulated at 2.33 ml/sec by using a water column to control the pressure. The heating block was maintained at 105° C. with a Barnant controller model 689 (Barrington, Ill.). Samples consisted of 20 ml of oil to which approximately 10 mg each of colloidal iron and copper were added. In some experiments only colloidal copper was added, and in other experiments the colloidal copper was replaced with various amounts of an ethanolic solution of cupric acetate. Samples (1 ml) of the soybean oil were withdrawn periodically and their viscosities were measured using a Brookfield LV–DV-II+ cone and plate viscometer (Stoughton, Mass.) operated at 40° C. After measuring the viscosity, the oil samples were returned to their respective AOM tubes. A value of 150 cP, which is an increase of about five times the viscosity of unoxidized soybean oil, was chosen as an arbitrary end point.

Initial isolation of EFAT. A column, 2 cm×54 cm, was filled with 120 ml hexane, and 150 g of 80–200 mesh alumina, which had been activated at 260° C. for 15 h (8), was added and allowed to settle under gravity. Ethylene glycol esters of soybean oil fatty acids (50 g) dissolved in 30 ml hexane were added, and the column was eluted with 240 ml hexane, 120 ml hexane-ethyl acetate (7:5, v:v), and 180 ml methanol. The eluate was collected in 20-ml portions, each of which was checked for its composition by thin-layer chromatography (TLC). The purified ethylene glycol diacyl esters were tested for their oxidative stability, and the EFAT isolate was tested for its ability to confer oxidative stability on ethylene glycol esters and soybean oil.

Thin-layer chromatography. Mixtures produced by ester syntheses (50 mg) were applied to Adsorbisil-Plus 1 silica thin-layer TLC plate 20×20 cm, 0.5 mm thickness (Altech Assoc., Deerfield, Ill.) with a streaker (Applied Science Laboratories, Inc., State College, Pa.). The plate was developed with hexane-ethyl ether-acetic acid (70:30: 1, v:v:v), and the components were visualized by spraying lightly with 0.1% (w/v) 2',7'-dichlorofluoresein (Sigma Chemical Co., St Louis, Mo.) in methanol. Silica containing visible bands was collected, and each band was extracted repeatedly with freshly distilled ethyl ether. The ether was evaporated and the residues were weighed and used for further analysis.

Gas chromatography (GC). The GC was a Hewlett-Packard (HP) 5890 Series II instrument with an HP3396 Series If integrator and FID detector. Two columns were used, a SUPELCO SPB-1, 30 m×0.25 mm ID, 0.25 $\mu$m film or a SUPELCO SP-2330,15 m×0.25 mm ID, 0.20 $\mu$m film. The SPB-1 column was operated with an injector temperature 280° C., detector temperature 300° C., initial column temperature 140° C. for 4 min, programmed at 5° C./min to 300° C., and held 6 min. For the SP2330 column the injector and detector temperatures were 250° C. and initial column temperature was 170° C. for 3 min, programmed at 20° C./min to 225° C. and held 6 min. For both columns the helium carrier flow was 1.5 ml/min, and other gases were at the setting recommended by the manufacturer.

GC/mass spectrometry (MS). For electron ionization MS an HP 5890 Series II instrument with an HP 5790 mass detector was used. The column was an SPB-1 as before. Injector and detector temperatures were 320° C.; initial oven temperature was 170° C. for 3 min and programmed at 10° C./min to 320° C. and held 6 min. The injector purge was turned on at 1 min, and helium flow was 1.5 ml.

For atmospheric pressure chemical ionization (APCI) a Finnigan JSQ 700 (Finnigan Instruments Corp., San Jose, Calif.) mass spectrometer fitted with a Finnigan APCI ion source was used. Samples were injected in the loop injection mode. First, the mass spectrometer was used in a single MS mode using the first quadrupole only with the second and third quadrupoles in the radio frequency only (RF) mode. The first quadrupole was scanned from ml/z 50 to m/z 700 at a rate of 1.2 second per scan. Next the mass spectrometer was used in an MS-MS mode, both first and third quadrupoles were used, and the second quadrupole was in RF mode. The vaporizer temperature was maintained at 400° C. in all experiments.

For exact mass MS a Kratos MS-50 double-focusing magnetic sector mass spectrometer (Kratos Instruments, Manchester, UK) was used, with a solid probe introduction, electron ionization mode, and manual peak matching at 10,000 resolution (10% valley definition) with pcrfluorokerosene as the reference compound.

Quantification of EFAT. The amount of toluenesulfonate esters in various preparations was determined by dissolving them in acetonitrile (HPLC grade) and determining the absorbance at 273 nm with a Hitachi TU-2000 Spectrophotometer (Hitachi Instruments, Inc., Conroe, Tex.).

EFAT also was quantified by using a GC to determine the amount of acyl group it contained. EFAT preparations were fractionated by TLC, and the EFAT band was recovered from the TLC plates and converted to methyl esters by reaction with 5.4 M methanolic sodium methoxide at room temperature for 1 h (9). Water was added to stop the reaction, and the methyl esters were extracted with 1 ml hexane; 0.1 ml of a methanolic solution containing methyl heptadecanoate was added as an internal standard, and the sample was adjusted to 1–2 mg/ml for analysis by GC.

To follow the synthesis of EFAT, 0.05 moles each of ethylene glycol, lauric acid, and TSA were esterified as before. Samples of about 0.3 g were taken periodically, washed with water to remove unreacted TSA and ethylene glycol, and the benzene was evaporated. The residue was weighed and dissolved in acetonitrile to give a concentration of about 1 mg/ml. Dibenzyl (1 mg/ml) was added as an internal standard. About 20 μl of sample was injected into a Shimadzu LC600 instrument with an SPD-6 AV ultraviolet detector (Kyoto, Japan). The column was a Zorbax SB-C18 4.6×25 mm (Agilent Technologies, Palo Alto, Calif.), and the mobile phase was acetonitrile at 1 ml/min. The eluate was monitored at 273 nm. The absorbance ratio of lauric EFAT (purified by TLC) to dibenzyl was established from the slope of absorbance versus concentration at 273 nm for the two compounds. The amount of ethylene glycol dilaurate was determined by GC, using methyl heptadecanoate as an internal standard and an SP-2330 column. The data were corrected for the relative response of the diesters and standard.

Proton Nuclear Magnetic Resonance (NMR). Measurements were carried out at room temperature using a Varian VXR-300 instrument. CDCl3 (d=7.26 ppm) was used as solvent and reference standard.

Peroxide decomposition. To test EFAT's effect on hydroperoxides, four 20-ml soybean oil samples that were approximately 1 mM in cupric acetate were oxidized in the AOM apparatus at 40° C. for 26 h. Laurie EFAT was added at 5% by weight to two of the samples, and the other samples served as controls. The sample and control oils were gassed with nitrogen for the remainder of the experiment. Samples were taken periodically, and their peroxide values were determined by the Stamm method (10).

Results

We tested the relative rates of oxidiation of methyl, ethylene glycol, and glycerol esters of soybean oil fatty acids to test the hypothesis that more fatty acids per molecule would increase the rate of polymerization. FIG. 1 shows the relative rates of viscosity increase of methyl, ethylene glycol, and glycerol esters of soybean oil fatty acids in the presence of added colloidal copper. Ethylene glycol esters increased in viscosity much slower than methyl esters, contrary to our hypothesis. The addition of colloidal iron had little effect on the oxidation of the esters, but copper markedly slowed the oxidation of both methyl esters and ethylene glycol esters while having a minimal effect on the glycerol esters. The addition of copper to lubricants has been advocated to slow oxidation (11).

Figure 2:
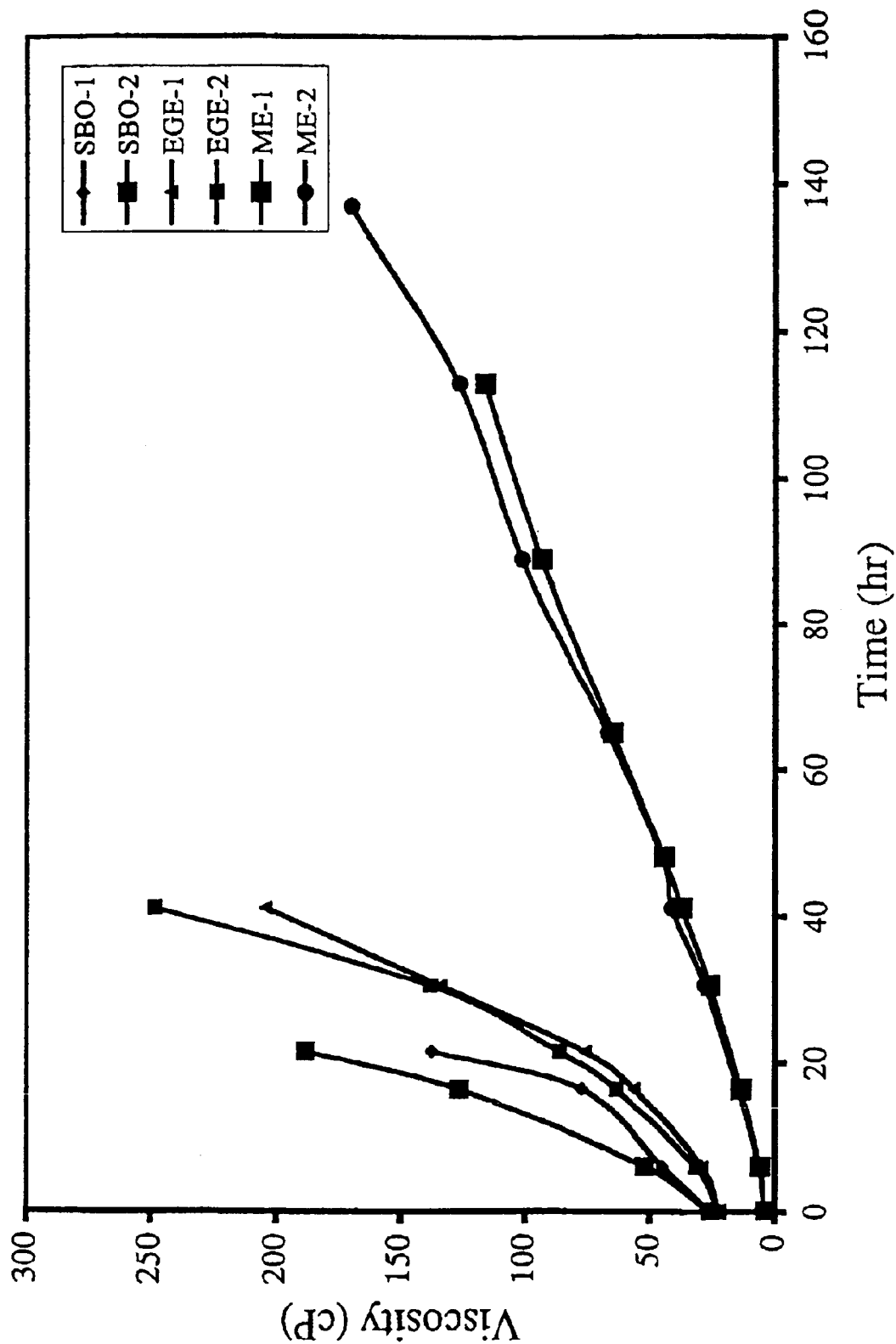
FIG. 2 shows change in viscosity with time of SBO and ME and EGE made with soybean oil fatty acids all of which had been purified by alumina chromatography. Conditions as in FIG. 1.
Figure 3:
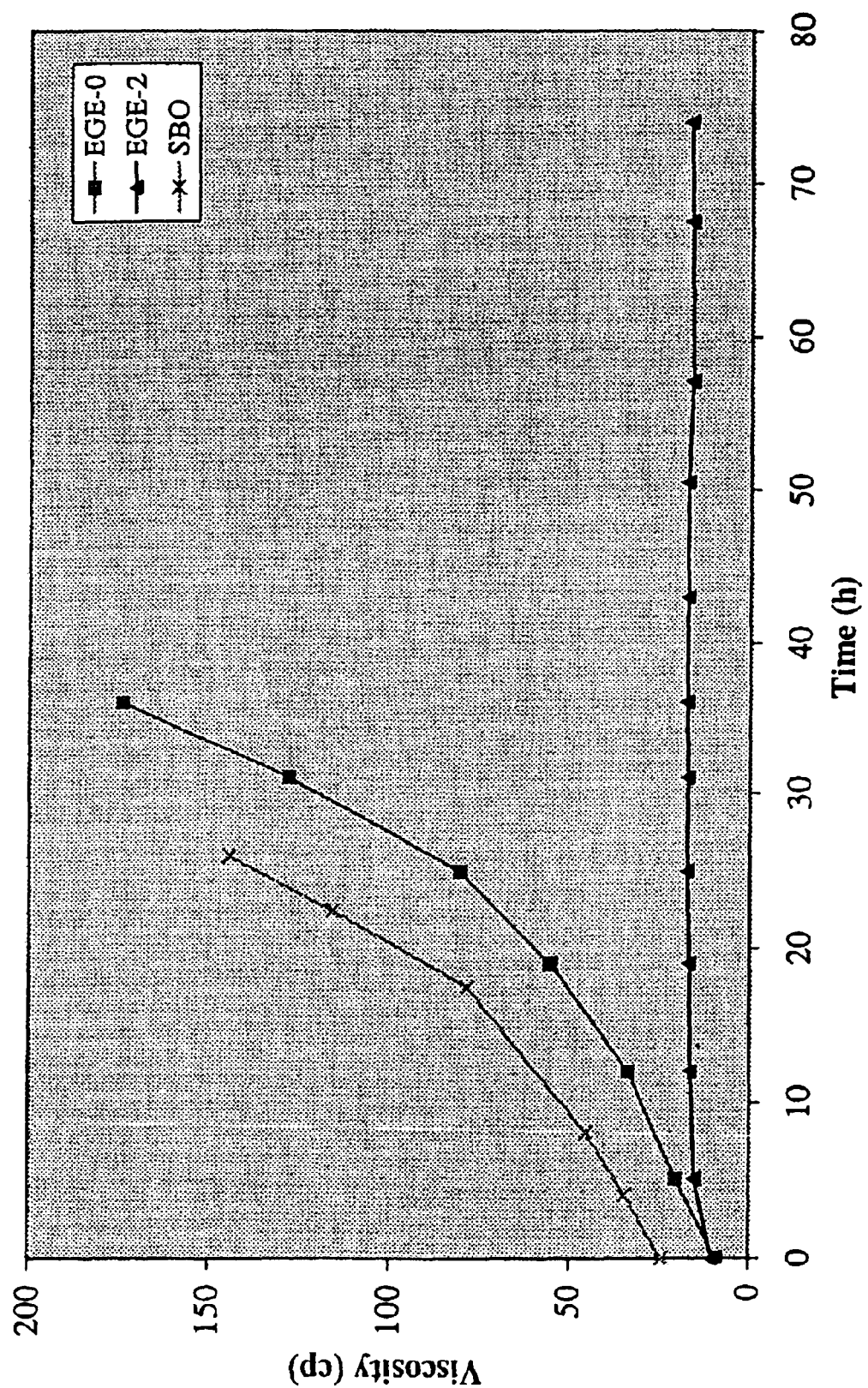
FIG. 3 shows change in viscosity with time of SBO and EGE made from soybean oil fatty acids and purified with alumina (EGE-0) and purified EGE with the two unknown materials isolated by alumina chromatography added back (EGE-2). Conditions as in FIG. 1.

To understand the unexpected stability of the ethylene glycol ester we subjected it to TLC and discovered three components of Rf 0.7, 0.3, and 0.2. The main component was that diacyl ester of Rf 0.7. The ethylene glycol ester mixture was fractionated on an alumina column to obtain enough material for our oxidation tests. FIG. 2 shows the relative stability in the AOM test with glycerol, ethylene glycol and methyl esters of soybean oil that all had been purified by chromatography on alumina. The results are more nearly what our hypothesis predicted. But when the material of Rf 0.3 and 0.2 were added back to ethylene glycol esters they greatly enhanced the esters' stability (FIG. 3). Similar effects were obtained when these unknown components were added to soybean oil (data not shown).

The component of Rf 0.2 was the monoacyl ester of ethylene glycol and was the primary component of reaction mixtures that had a high ratio of ethylene glycol to fatty acid. By itself it had no effect on oil stability. The unknown component of Rf 0.3 was treated with methanolic sodium methoxide and GC on an SPB 2330 column revealed the presence of methyl esters of the fatty acids of soybean oil. By refluxing palmitic, oleic, linoleic, and linolenic acids individually with ethylene glycol and TSA and removing water of esterification as a benzene azcotrope, material analogous to the unknown spot was obtained but with only one kind of acyl group.

The unknown containing linolenate was chosen for further study by GC/MS. By electron impact GC/MS there was one major component with its mass fragments at 99 (100) 55 (74) 139 (20) 79 (20) 67 (17) 91 (18) 112 (18) 153 (16) 86 (9) 125 (9). The patent compound seemed to have a molecular weight of 304, and the spectrum was consistent with a lactone formed from ethylene glycol monolinolenate by splitting out water from the free hydroxy group and a β-hydrogen from the linolenate. But lactones were not polar enough to account for the TLC properties of the unknown.

Figure 4:
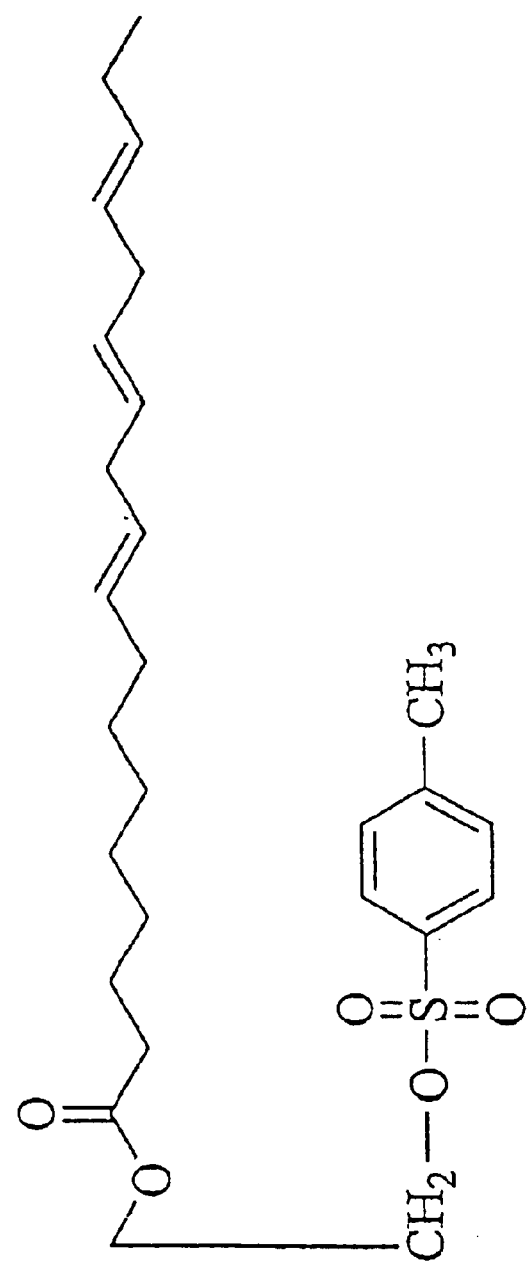
FIG. 4 shows the structure of ethanediol linolenatc p-toluenesulfonate, EFAT.

The APCI-MS of the unknown based on linolenate revealed peaks at 477 (100) 305 (46) 261 (18) 243 (04). This is consistent with a molecular weight of 476 with a major fragment at 304. The peaks at 305 and 261 were shown to be fragments of the 477 peak. This molecular weight is consistent with ethandiol p-toluenesulfonate linolenate. This structure was confirmed by exact mass measurement of the molecular weight as 476.26088, which was best fit $C_{27}H_{40}O_5S$. The exact mass spectrum also contained a strong peak at mass 91, indicating a toluene ring. We suggest the trivial name EFAT for the compound for ethylene, glycol, fatty acylate, and p-toluenesulfonate (FIG. 4).

Figure 5:
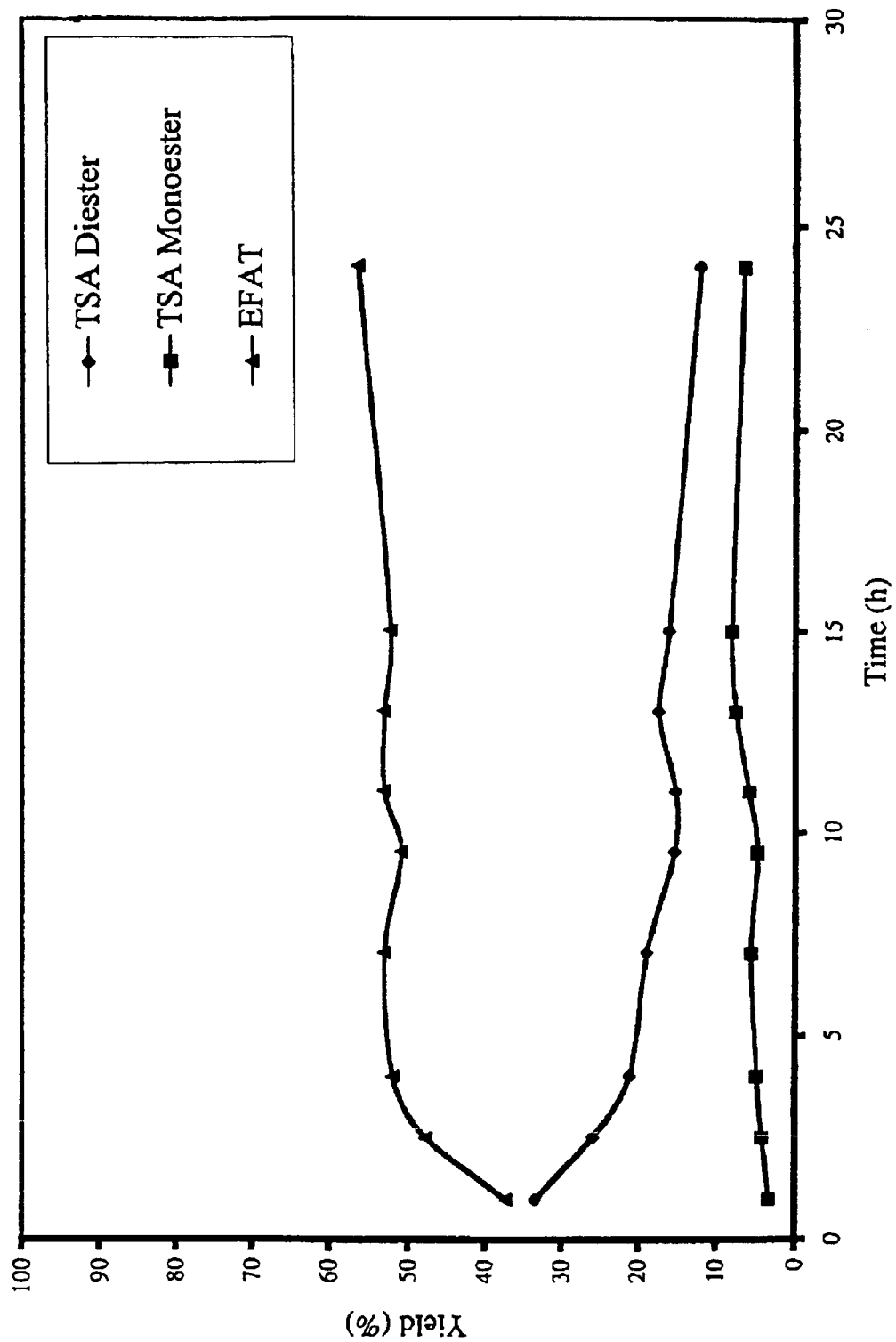
FIG. 5 shows the weight % yield of EFAT, ethylene glycol dilaurate, and ethylene glycol monoTSA versus time. Conditions: molar ratio of p-toluenesulfonic acid (TSA) :ethylene glycol:lauric acid 1:1:1 in refluxing benzene with water removal by a Dean-Stark trap.

The quantification of EFAT was achieved by transesterification of the acyl group to methyl ester and GC with an internal standard; by ultraviolet spectrophotometry at 273 nm, where TSA has a strong absorption peak; and by HPLC in acetonitrile monitored at 273 nm. Using these methods, we concluded that the concentration of EFAT in our original ethylene glycol esters was about 5%. This yield has been improved considerably by increasing the molar ratio of TSA to ethylene glycol and fatty acid to 1:1:1. When this ratio was used, the concentration of EFAT in the reaction mixture rose quickly to about 50% and then more slowly rose to about 60% as shown in FIG. 5. The formation of diacyl ester is faster and decreases with reaction time.

Figure 6:
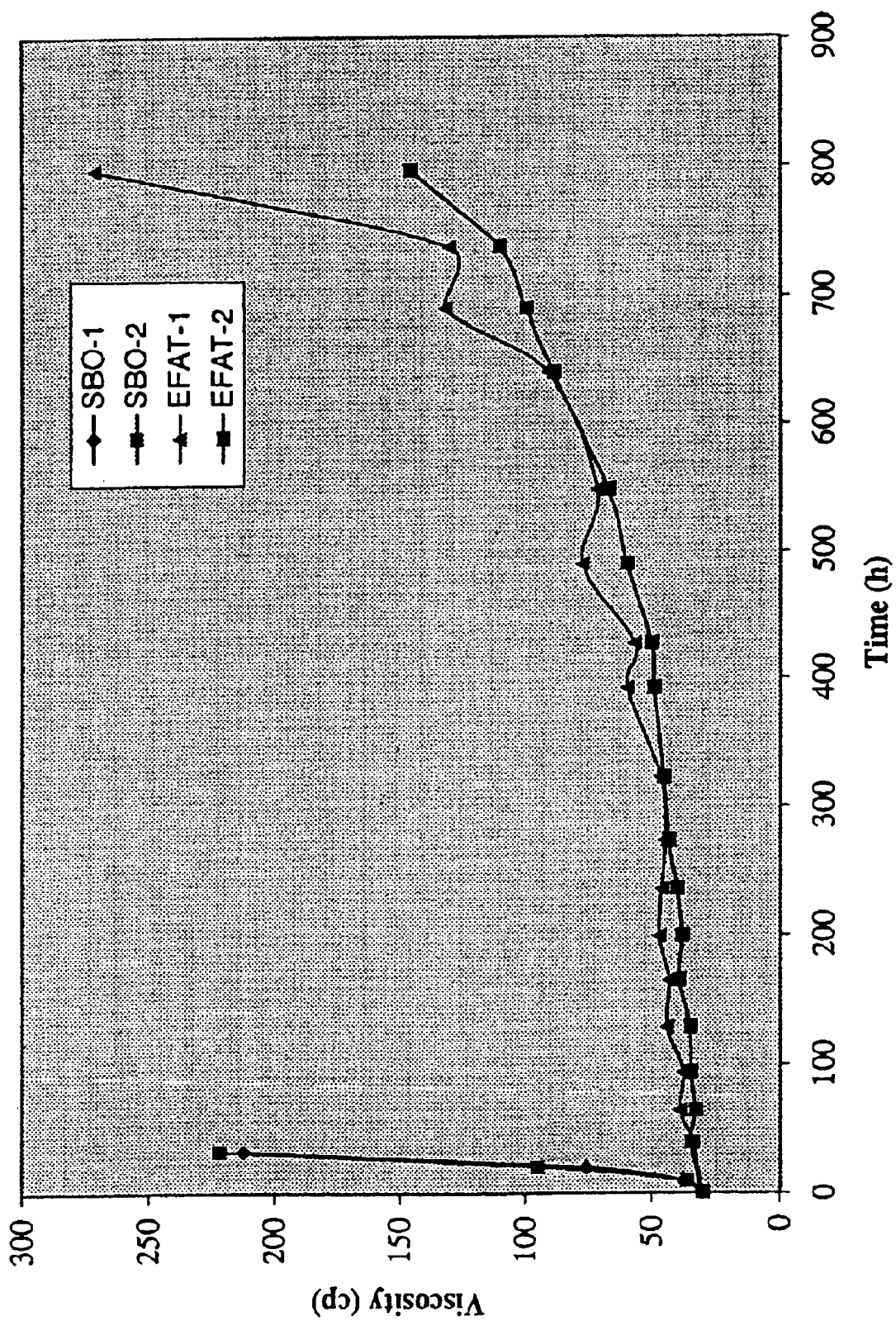
FIG. 6 shows change in viscosity with time of SBO and soybean oil stabilized with 5% EFAT. Conditions as in FIG. 1.

FIG. 6 shows the effect on the stability of soybean oil of 5% EFAT in which the acyl groups were soybean oil fatty acids. The viscosity of the soybean oil with EFAT slowly rose to 150 cp in about 800 h compared with about 25 h for the control. EFAT is much more effective in stabilizing the oil than TBHQ-citric acid, which was the best antioxidant reported by Ruger and Hammond (6). But the ability of EFAT to prevent the polymerization of soybean oil requires a fairly high concentration compared with other antioxidants. EFAT had no antioxidant activity at 1%, and may have a slight prooxidant effect.

Modifications of EFAT. Various modifications in the structure of EFAT were tried to determine the structural features required for antioxidant activity. Using the same synthesis used to make EFAT with soybean oil fatty acids as the acyl groups, we used purified fatty acids as short as lauric acid to alter the acyl group in EFAT. All of these acyl group variations were active in stability tests. When we tried octanoic acid, most of it was distilled with the benzene azeotrope and was lost, so the yield was too poor for testing.

Mono alcohol esters of TSA were tested. Ethyl p-toluensulfonate was purchased, and decyl p-toluensulfonate was made using benzene azeotrope distillation. Both gave no antioxidant activity in our modification of the AOM test when tested at the 5% level.

EFAT analogs were synthesized using glycerol and 1,2- and 1,3-propylene glycol in place of ethylene glycol. The structures of the later two products were verified by MS and NMR. Chemical shifts for the propylene glycol esters are given in ppm($\delta$), and multiplicities are indicted by s (singlet), d (doulblet), t (triplet), q (quartet), p (pentalet) and m (multiplet). $^1$H NMR (300 Mhz, CDCl3, 16 mg/ml) for the 1,2-propylene glycol product $\delta$: 0.87 (3H, t), 1.30 (22H, s), 2.16 (2H, m), 2.45 (3H, s), 4.03 (2H, m), 4.91 (1H, m), 7.35 (2H, d), 7.79 (2H, d). For the 1,3-propylene glycol product $^1$H NMR (300 Mhz, CDCl3, 16 mg/ml) $\delta$: 0.88 (3H, t), 1.25 (18H, s), 1.98 (2H, p), 2.21 (2H, t), 2.45 (3H, s), 4.09 (4H, m), 7.35 (2H, d), 7.79 (2H, d). The two spectra are similar. The major difference is that the 1,3-isomer had a methylene group in the middle of 1,3-propylene glycol backbone that gave a pentalet at 1.98 ppm, and the two methylene group adjacent to ester bond gave two joint triplets at 4.09 ppm. For the 1,2-isomer the methyl group at the end of 1,2-proplyene glycol joined with methylene groups on the fatty acid chain at 1.25 ppm, and the —CH group in the middle of the propylene glycol gave a multiplet near 4.91 ppm. This multiple arose because the product is a mixture of two compounds that vary in the position of tosyl and lauryl groups. The 1,3-propylene glycol product gave APCIMS peaks at 413, 241, 104, 183, and 445 using hydrogen as the ionizing gas. The peak at 413 is the expected mass+one. The 241 fragment is produced by the loss of the tosyl group. The 183 fragment probably comes from the lauryl group split between its ester oxygen and carbonyl group. For the 1,2-ethylene glycol product no peak representing the intact molecule was obtained; only the 241 peak resulting from the loss of the tosyl group was observed.

The EFAT made with glycerol and 1,2-propylene glycol were active as antioxidants in the modified AOM test at the 5% level. The EFAT made from 1,3-propylene glycol was not (data not shown). These results suggest that for antioxidant activity the EFAT must have its acyl group and tosyl groups on adjacent carbons.

EFAT was made with sodium dodecylbenzenesulfonate in place of TSA. The sodium salt was neutralized with sulfuric acid and esterified with ethylene glycol and lauric acid as usual. The APCIMS of this product ionized with hydrogen gave peaks at 401, 227, and 353. None of these represented the intact molecule, but the 227 peak represents the loss of the dodecylbenzenesulfonyl group, and the 353 peak represents the loss of the lauryl chain. This version of EFAT was active as an antioxidant in the modified AOM test at the 5% level (data not shown).

FIG. 7 shows that when free TSA was tried in the modified AOM test it prolonged the time for viscosity increase to 150 cp from about 30 h to 150 h. But TSA itself is an interesterification catalyst and may react with soybean oil under AOM conditions to form a glycerol-based version of EFAT. The figure also shows that if ethylene glycol and free fatty acids are put into the reaction mixture, an antioxidant effect is observed that is better than that of TSA alone but not as great as that of preformed EFAN. These observations suggest that EFAT is formed to some extent during the AOM test. If no source of hydroxy groups is present, EFAT formation may be limited to the amount of mono- and diglycerides in the test oil.

Figure 8:
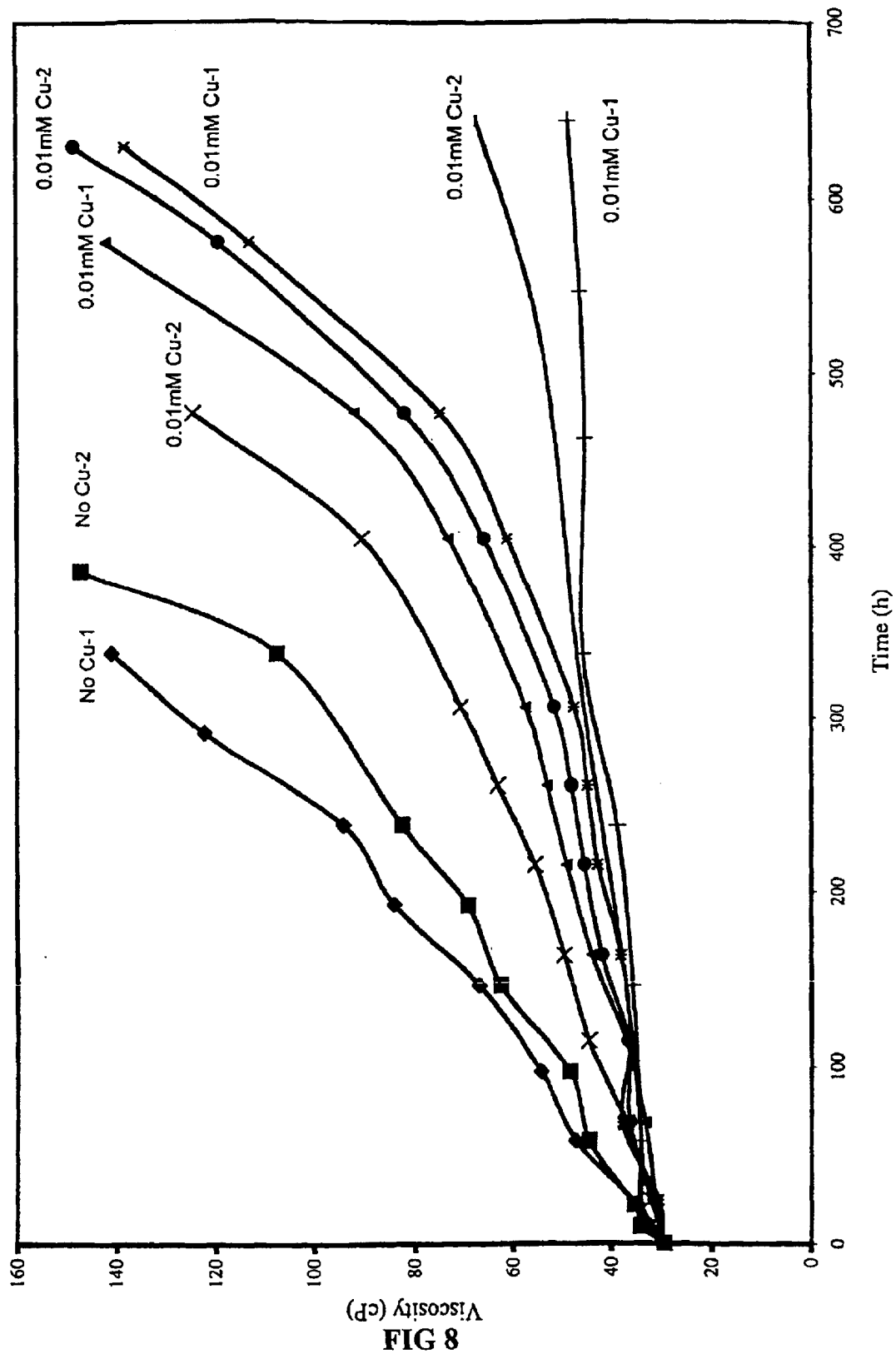
FIG. 8 shows change in viscosity with time of soybean oil with 5% EFAT in the presence of various molar concentrations of cupric acetate.

The level of copper needed. Cupric acetate could successfully replace colloidal metallic copper in the modified AOM stability test, so presumably the colloidal copper metal was furnishing cupric ions. The use of cupric acetate made it possible to measure the amount of copper ion needed. FIG. 8 shows that with no added cupric ion and 5% EFAT, the AOM time was reduced to about 300 h rather than the 800 h observed with colloidal copper metal. Increasing levels of copper ion from 0.01 mmolar up to about 1.1 mmolar or about 76 ppm increased the AOM time, and at 1.1 mmolar the AOM time was about as long as that with the colloidal copper metal. The copper content of the refined soybean oil has been reported to be about 0.02 to 0.06 ppm (12), which would be about 0.001 mmolar. EFAT at 2% in the oil is about 41 mmolar, which is about 37.5 times greater than the moles of copper necessary to give good stability.

Figure 9:
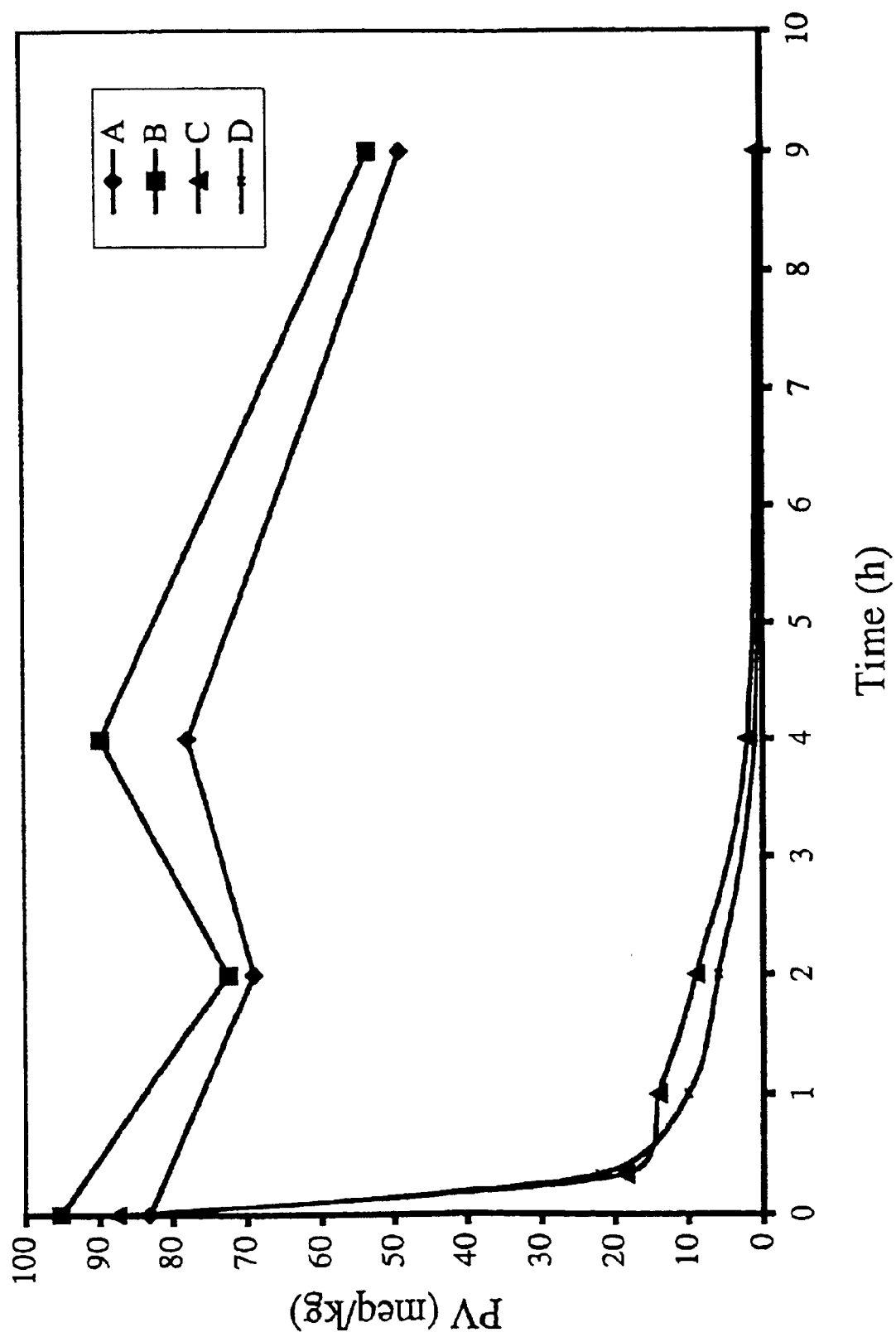
FIG. 9 shows decomposition of soybean oil hydroperoxides in soybean oil that was 1 mM in cupric ion versus time under nitrogen at 40° C. Curves A and B are controls with no EFAT; C and D contain 5% EFAT.

Effect of EFAT on hydroperoxides. FIG. 9 shows that the addition of EFAT to oxidized soybean oil samples held under nitrogen at 40° C. caused a much more rapid decrease of peroxide value than controls. These results agree with our observation that samples of soybean oil containing EFAT never accumulate as much peroxide as controls during AOM testing. These results suggest that EFAT exerts its antioxidant action by destroying peroxides and thus reducing the rate of free radical initiation. Normally the thermal decomposition of hydroperoxides in the presence of oxygen leads to the formation of free radicals that result in further accumulation of hydroperoxides.

The present invention is not intended to be limited to the foregoing example, but encompasses all such modifications and variations as come within the scope of the appended claims.

REFERENCES

1. United Soybean Board. 1997. Market opportunity summary for soy-based lubricant.
2. United Soybean Board. 1998. Soil oil lubricants to be made in Michigan; *Feedstocks, News About Industrial Products Made From Soy*, Volume 3, Issue 4.
3. Agriculture-Based Industrial Lubricants. 1999a. UNI-developed soy lubricants garners praise from Department of Energy; *ABIL Advocate*, Volume 2, No. 2, Neuzil D. I. ed.
4. Agriculture-Based Industrial Lubricants. 1999b. UNI-ABIL field test activities: updates and initiatives; *ABIL Advocate*, Volume 2, No. 2, Neuzil D. I. ed.
5. Lawate, Saurabh and Glancey, Jim. 1998. Persented at: *Lubricants and Fluids Technical Advisory Panel.*
6. Ruger, C. W., Stabilizing Soybean Oil for Industrial Uses, M. S. Thesis, Iowa State University, Ames, Iowa (1999).
7. American Oil Chemists' Society, Official Methods and Recommended Practices of the American Oil Chemists' Society, 4th edn., AOCS Press, Champaign, 1993, Cd12–57.
8. Jensen, R. G., T. A. Marks, J. Sampugna, J. G. Quinn and D. L. Carpenter, Purification of Triglycerides with an Alumina Column, Lipids 1:451–452 (1966).
9. Hammond, E. G., Rapid analysis of lipids in many individual plants, in Modern Methods of Plant Analysis, New Series, Vol. 12, edited by H. F. Liskens and J. F. Jackson, Springer-Verlag, New York, 1991, pp. 321–330.
10. Hamm, D. G., E. G. Haammond, V. Parvanah, and H. E. Snyder, The Determination of Peroxides by the Stamm Method. J. Am. Oil Chem. Soc. 42: 920–922 (1965).
11. Garmier, W. W., Biodegradable Lubricant Composition from Triglycerides and Oil-Soluble Copper, PCT Int. Appl. WO 9743361 (1997).
12. List, G. R., Special Processing for Off Specification Oil, in Handbook of Soy Oil Processing and Utilization, edited by D. R. Erickson, E. H. Pryde, O. L. Brekke, T. L. Mounts, and R. A. Falb, American Oil Chemists' Society, Champaign, Ill., 1980, pp. 355–376.

We claim:

1. A composition comprising a compound of the formula:

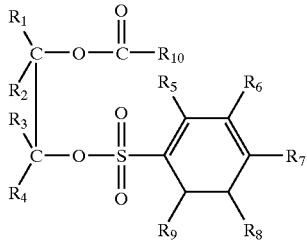

wherein $R_1$–$R_{10}$ are selected from the group consisting of hydrogen and a carbon chain, wherein the carbon chain is saturated, unsaturated, linear, branched, cyclic, or polycyclic and can have heteroatoms attached; wherein $R_1$ and $R_2$ are hydrogen and $R_{10}$ is a carbon chain of one to 30 carbons when $R_{10}$ is not hydrogen.

2. The composition of claim 1, wherein $R_3$–$R_9$ are selected from hydrogen, an alkyl group, an alkenyl group, an alkynyl group, an alcohol group or an aromatic group wherein each of $R_5$–$R_9$ has less than 13 carbons; and $R_{10}$ is selected from hydrogen, an alkyl group, an alkenyl group, an alkynyl group and an alcohol group.

3. The composition of claim 1, wherein $R_1$ and $R_3$ are hydrogen; wherein $R_4$ is selected from the group consisting of hydrogen or and —$CH_2OH$, $R_{10}$ is an alkyl or alkenyl group of 10 to 18 carbons; and one of $R_5$–$R_9$ is hydrogen or an alkyl group of less than 13 carbons and the others are hydrogen.

4. The composition of claim 1 wherein the compound is an ethanediol fatty acylate p-toluenesulfonate.

5. The composition of claim 1, further comprising a copper-containing compound.

6. The composition of claim 5, wherein the copper-containing compound contains a divalent copper.

7. The composition of claim 5, wherein the copper-containing compound is colloidal metallic copper.

8. A composition comprising:
a fluid comprising at least one target molecule subject to oxidation in the fluid, the at least one target molecule being selected from a non-ester and an alcohol ester having an ester group on each of at least two adjacent carbons in the alcohol moiety; and
a compound of the formula

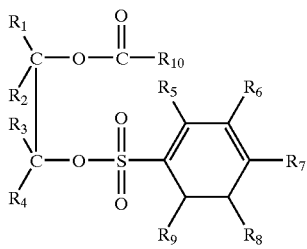

wherein $R_1$–$R_{10}$ are either hydrogen or a carbon chain that can be saturated, unsaturated, linear, branched, cyclic, or polycyclic and can have heteroatoms attached; the carbon chain of $R_{10}$ is of one to 30 carbons.

9. The composition of claim 8, wherein the fluid is an unsaturated triglyceride oil.

10. The composition of claim 9 wherein the unsaturated triglyceride oil is a vegetable oil.

11. The composition of claim 10 wherein the vegetable oil is soybean oil.

12. The composition of claim 8, further comprising divalent copper ions.

13. The composition of claim 12, wherein the divalent copper ion has a concentration of at least about 0.001 mM relative to the total volume of the at least one target molecule.

14. The composition of claim 12, wherein the divalent copper ion has a concentration of at least about 0.01 mM relative to the total volume of the at least one target molecule.

15. The composition of claim 12, wherein the divalent copper ion has a concentration of at least about 0.1 mM relative to the total volume of the at least one target molecule.

16. The composition of claim 12, wherein the divalent copper ion has a concentration of at least about 1.0 mM relative to the total volume of the at least one target molecule.

17. The composition of claim 8 wherein the composition is a lubricant.

18. The composition of claim 8 wherein the composition is a hydraulic fluid.

19. The composition of claim 8, wherein the compound has a concentration of at least about 40 mM relative to the total volume of the at least one target molecule.

20. The composition of claim 8, wherein the compound has a concentration of at least about 60 mM relative to the total volume of the at least one target molecule.

21. The composition of claim 8, wherein the compound of claim 1 has a concentration of at least about 100 mM relative to the total volume of the at least one target molecule.

22. A method for inhibiting oxidization of a at least one target molecule in a fluid, the at least one target molecule being subject to oxidation in the fluid and being selected from a non-ester and an alcohol ester having an ester group on each of at least two adjacent carbons in the alcohol moiety, the method comprising the step of adding into the fluid a compound of the formula

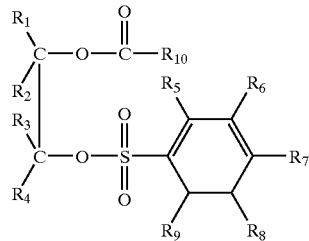

wherein $R_1$–$R_{10}$ are either hydrogen or a carbon chain that can be saturated, unsaturated, linear, branched, cyclic, or polycyclic and can have heteroatoms attached, the carbon chain of $R_{10}$ is of one to 30 carbons.

23. The method of claim 22 further comprising the step of adding a copper-containing compound into the fluid.

24. A composition comprising a copper-containing compound and a compound of the formula:

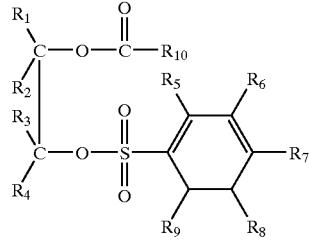

wherein $R_1$–$R_{10}$ are either hydrogen or a carbon chain that can be saturated, unsaturated, linear, branched, cyclic, or polycyclic and can have heteroatoms attached; and the carbon chain of $R_{10}$ is of one to 30 carbons.

25. The composition of claim 24, wherein the copper-containing compound contains a divalent copper.

26. The composition of claim 24, wherein the copper-containing compound is colloidal metallic copper.

27. A compound having a formula

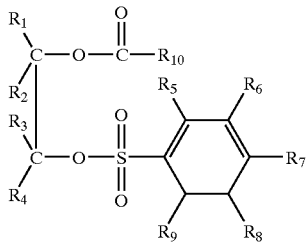

wherein $R_1$–$R_{10}$ are either hydrogen or a carbon chain that can be saturated, unsaturated, linear, branched, cyclic, or polycyclic and can have heteroatoms attached; $R_1$ and $R_2$ being hydrogen, $R_{10}$ being a carbon chain of one to 30 carbons when $R_{10}$ is not hydrogen.

28. The compound of claim 27, wherein $R_3$–$R_9$ are selected from hydrogen, an alkyl group, an alkenyl group, an alkynyl group, an alcohol group or an aromatic group wherein each of $R_5$–$R_9$ has less than 13 carbons; and $R_{10}$ is selected from hydrogen, an alkyl group, an alkenyl group, an alkynyl group and an alcohol group.

29. The compound of claim 27, wherein $R_3$ is hydrogen; wherein $R_4$ is selected from the group consisting of hydrogen and —$CH_2OH$, $R_{10}$ is an alkyl or alkenyl group of 10 to 18 carbons; and one of $R_5$–$R_9$ is hydrogen or an alkyl group of less than 13 carbons and the others are hydrogen.

30. A fluid comprising:
at least one target molecule subject to oxidation in the fluid and being selected from a non-ester and an alcohol ester having an ester group on each of at least two adjacent carbons in the alcohol moiety; and
a compound of the formula

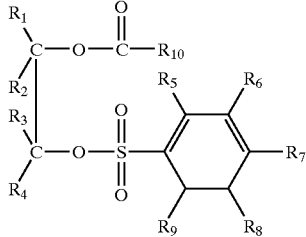

wherein $R_1$–$R_{10}$ are either hydrogen or a carbon chain that can be saturated, unsaturated, linear, branched, cyclic, or polycyclic and can have heteroatoms attached; the carbon chain of $R_{10}$ is of one to 30 carbons.

31. The composition of claim 30, the at least one target molecule being an unsaturated triglyceride oil.

32. The composition of claim 31 wherein the unsaturated triglyceride oil is a vegetable oil.

33. The composition of claim 32 wherein the vegetable oil is soybean oil.

34. The composition of claim 30 wherein the composition is a lubricant.

35. The composition of claim 30 wherein the composition is a hydraulic fluid.

36. The composition of claim 30 wherein the compound has a concentration of at least about 40 mM relative to the volume of the at least one target molecule.

37. The composition of claim 30, wherein the compound has a concentration of at least about 60 mM relative to the volume of the at least one target molecule.

38. The composition of claim 30, wherein the compound has a concentration of at least about 100 mM relative to the volume of the at least one target molecule.

39. The composition of claim 30, further comprising divalent copper ions.

40. The composition of claim 39, wherein the divalent copper ions are present at a concentration of at least about 0.001 mM relative to the volume of the at least one target molecule.

41. The composition of claim 39, wherein the divalent copper ions are present at a concentration of at least about 0.01 mM relative to the volume of the at least one target molecule.

42. The composition of claim 39, wherein the divalent copper ions are present at a concentration of at least about 0.1 mM relative to the volume of the at least one target molecule.

43. The composition of claim 39, wherein the divalent copper ions are present at a concentration of at least about 1.0 mM relative to the volume of the at least one target molecule.

* * * * *